US012741809B2

(12) United States Patent
Boye et al.

(10) Patent No.: US 12,741,809 B2
(45) **Date of Patent: *Sep. 22, 2026**

(54) SANITARY DEVICE AND PEST PREVENTION DEVICE FOR GARBAGE CAN LIDS

(71) Applicant: GROTE Industries LLC, Oneida, WI (US)

(72) Inventors: Keith R. Boye, Oneida, WI (US); Robert Godfrey, Monona, WI (US); Jared Miller, Deforest, WI (US); Jeffrey J. Brickl, Prairie Du Sac, WI (US)

(73) Assignee: GROTE Industries LLC, Oneida, WI (US)

( * ) Notice: Subject to any disclaimer, the term of this patent is extended or adjusted under 35 U.S.C. 154(b) by 47 days.

This patent is subject to a terminal disclaimer.

(21) Appl. No.: 18/887,338

(22) Filed: Sep. 17, 2024

(65) Prior Publication Data

US 2025/0011080 A1 Jan. 9, 2025

Related U.S. Application Data

(63) Continuation-in-part of application No. 18/223,317, filed on Jul. 18, 2023, now Pat. No. 12,371,255.

(Continued)

(51) Int. Cl.
*B65F 7/00* (2006.01)
*A01M 29/12* (2011.01)

(Continued)

(52) U.S. Cl.
CPC ............... *B65F 7/00* (2013.01); *A01M 29/12* (2013.01); *A61L 2/22* (2013.01); *A61L 2/26* (2013.01);

(Continued)

(58) Field of Classification Search
CPC .. A01M 29/12; A61L 2/22; A61L 2/26; A61L 2202/15; A61L 2202/16;

(Continued)

(56) References Cited

U.S. PATENT DOCUMENTS

| | | | | |
|---|---|---|---|---|
| 12,371,255 | B2 * | 7/2025 | Boye | B05B 1/12 |
| 2006/0289679 | A1 * | 12/2006 | Johnson | B05B 1/3046 222/333 |
| 2015/0122813 | A1 * | 5/2015 | El-Taher | B65F 1/1607 220/87.2 |

FOREIGN PATENT DOCUMENTS

| | | |
|---|---|---|
| CN | 111689091 A | 9/2020 |
| JP | 2000062904 A | 2/2000 |
| KR | 200397074 U | 9/2005 |

* cited by examiner

*Primary Examiner* — Douglas Lee
(74) *Attorney, Agent, or Firm* — Wong Meyer Smith & McConnell

(57) ABSTRACT

Systems and methods for sanitizing, cleaning, and deodorizing the interior of a garbage can are provided, as well as deterring pests from entering the garbage can or terminating pests that do enter the garbage can. A device is provided that includes a housing and an adjustable nozzle configured to dispense a cleaning solution into the interior of the garbage can. Additionally, the device includes a power source such as a battery, as well as an electronic board that can enable and disable the nozzle. The device can be mounted to an underside of a lid of the garbage can, which allows solution to be sprayed downwardly into the interior of the garbage can and bags contained therein. The adjustable nozzle can be adjusted to a number of different spray patterns. When the solution of the device is depleted, it can be replaced for further use of the device.

20 Claims, 14 Drawing Sheets

Related U.S. Application Data

(60) Provisional application No. 63/390,042, filed on Jul. 18, 2022.

(51) Int. Cl.
*A61L 2/22* (2006.01)
*A61L 2/26* (2006.01)
*B08B 9/08* (2006.01)
*B65F 1/04* (2006.01)
*B65F 1/14* (2006.01)

(52) U.S. Cl.
CPC .............. *B08B 9/0804* (2013.01); *B65F 1/04* (2013.01); *B65F 1/14* (2013.01); *A61L 2202/15* (2013.01); *A61L 2202/16* (2013.01); *A61L 2202/17* (2013.01); *B08B 2209/08* (2013.01)

(58) Field of Classification Search
CPC ... A61L 2202/17; A61L 9/14; B08B 2209/08; B08B 9/0804; B65F 1/04; B65F 1/14; B65F 7/00
See application file for complete search history.

SANITARY DEVICE AND PEST PREVENTION DEVICE FOR GARBAGE CAN LIDS

CROSS-REFERENCE(S) TO RELATED APPLICATION(S)

This present application is a continuation-in-part application claiming priority to U.S. Non-Provisional patent application Ser. No. 18/223,317 filed on Jul. 18, 2023 and entitled Sanitary and Pest Prevention Device for Garbage Can Lids, which claims priority on U.S. Provisional Patent Application Ser. No. 63/390,042, filed on Jul. 18, 2022 and entitled Sanitary Device for Garbage Can Lids, the entire contents of which are hereby expressly incorporated by reference into the present application.

BACKGROUND OF THE INVENTION

1. Field of the Invention

The invention relates generally to garbage cans and, in particular, to a sanitary device that can be mounted to a portion of the garbage can, for instance the lid, to improve sanitization, reduce bacteria and germ growth, and reduce odor, within the garbage can, as well as deter pests from entering the garbage can or dispel of pests that have entered the garbage can. More specifically, the invention relates to a sanitary device, such as a puck, that is mounted to the underside of the top lid of an outdoor garbage can that is configured to periodically spray a disinfecting and/or scented mist to improve the smell of the interior of the trash can while killing germs, bacteria, and other microorganisms that may be present within the container. Additionally, the device may be configured to spray a material that deters pests, such as rats, racoons, bugs, maggots, larva, flies, and the like from entering the garbage can, or dispel of such pests that have already entered the garbage can.

2. Discussion of the Related Art

Despite best efforts to keep areas in and around garbage or trash cans, dumpsters, or other containers clean, they inevitably get dirty. Outdoor garbage cans and dumpsters are oftentimes even worse than indoor garbage cans in terms of their cleanliness and smell. Because they are located outdoors, users are less likely to take issues with messes located within the can. For instance, even when a garbage bag from an indoor can breaks, users nevertheless throw the broken bag directly into the outdoor garbage can, causing the contents of the bag to fall out of the bag and into the bottom of the outdoor can. Similarly, animals smelling food or other waste products can rip open bags causing the contents to fall out. This can include rats, mice, racoons, and other animals. Other pests, such as bugs including maggots, larva, and flies, also may enter the garbage can, particularly when waste is exposed within the garbage can.

Additionally, because they are outside, outdoor cans are exposed to the elements, which can include warm temperatures and sunlight, which can lead to increased spreading of germs, bacteria, other microorganisms, and associated smells. Even when an "outdoor" garbage can is located in a garage, it can still be subject to adverse elements, while also being in closer proximity to individuals, as well as vehicles, garage refrigerators or freezers, and the like. Further still, outdoor garbage cans and dumpsters are emptied on a less frequent basis than indoor garbage cans, such that filled garbage bags can remain within the can for days or even weeks. Furthermore, certain waste materials are exclusively deposited into an outdoor can, including pet waste and other chemical materials. This causes the smell associated with outdoor garbage cans and dumpsters to usually be even worse than indoor garbage cans. In addition to the displeasure associated with smelly and gross garbage cans, there is concern for growth of bacteria and other microorganisms that can be dangerous for humans and animals living in close proximity to the garbage can.

To remedy these issues, typically users would need to open the garbage can and manually spray a cleaning solution into the can. This can be unappealing, time-consuming, and easy to forget. Additionally, some individuals hire steam cleaners who come on an annual or biannual basis to steam these cans. While better than nothing, these cleanings are infrequent and thus not sufficient to fully address the underlying issues. Another common issue is that when garbage cans go uncleaned, pests including animals as well as bugs may enter and in some instances live within the garbage can.

What is therefore needed is a device to help minimize the growth and spread of odors, as well as germs, bacteria, and microorganisms located within a garbage can, and more specifically an outdoor garbage can or dumpster. What is further needed is a device that periodically dispenses materials to help reduce the growth and spread of odors, germs, bacteria, and microorganisms located within a garbage can or dumpsters. Additionally, what is needed is a device that deters or dispels pests, such as animals and bugs, from entering or living within a garbage can. U.S. Patent Application Publication No. 2022/0112030 published on Apr. 14, 2022 addressed a number of these issues, and its contents are incorporated herein by reference.

SUMMARY AND OBJECTS OF THE INVENTION

By way of summary, the present invention is directed to a sanitization device for a garbage can, dumpster, or other container (collectively referred to as garbage cans herein). More specifically, the present invention is directed to a sanitization device including a housing and a container containing a cleaning or other solution and a sprayer associated with the housing that dispenses cleaning solution into the garbage can.

According to an aspect of the present invention, the sprayer may further include an adjustable nozzle that has two or more different spray patterns. For instance, the nozzle may have a wide spray pattern and a narrow spray pattern. In the wide spray pattern, a spray cone of approximately 70 degrees may be achieved, and in the narrow spray pattern, a spray cone of approximately 20 degrees may be achieved. Further still, the nozzle may include a third medium spray pattern, with that spray pattern having a spray cone of approximately 40 degrees.

According to another aspect of the present invention, the adjustable nozzle may have a first channel and a second channel. Additionally, the adjustable nozzle may have a first orifice that is in fluid flow connection with the first channel and a second orifice that is in fluid flow connection with the second channel. In certain embodiments, the orifices may be formed in first and second plugs that are inserted into openings formed in an underside of the adjustable nozzle body. Solution directed through the first channel and out the first orifice has a first spray configuration, such as a wide spray pattern, whereas solution directed through the second channel and out the second orifice has a second spray configuration, such as a narrow spray pattern. Additionally, the device may be configured to perform multiple sprays depending on the channel through which the solution is directed, such as three spray pulses from the first orifice and two spray pulses from the second orifice.

According to another aspect of the present invention, the device may further include a container that contains the cleaning solution, where the adjustable nozzle has a base that is secured to the container and a side plate that is rotatably connected to the base. The side plate may be rotated relative to the base about three positions having three spray patterns. Further still, the device may include a tab that is configured to hold the container in place relative to the housing. Further still, a delivery tube may be used with the container. The container may include a reservoir that holds the cleaning solution, where the reservoir is a substantially horizontally mounted reservoir, although a bottom wall of the reservoir is slightly angled towards a low point. The tube extends downwardly from the adjustable nozzle to the bottom wall of the reservoir.

According to another aspect of the present invention, a pump may extend from the container, and a shaft may extend from the pump. The shaft is configured to be removably inserted into the first and second channels described above. In this way, the adjustable nozzle can be moved between different positions based on which channel the shaft is inserted into. This enables for quick and easy movement between different positions in which different spray patterns result.

According to another aspect of the present invention, the device includes a housing that contains a solution, such as a cleaning solution, as well as a sprayer that is contained within the housing the is configured to dispense the cleaning solution into the interior of the garbage can. By way of example and not limitation, the cleaning solution could be ZETRISIL, made by ESC Brands. Additionally, or alternatively, the solution may be configured to deter pests, such as animals, insects, and the like, from entering the garbage can, or to terminate pests once they enter the garbage can. The housing can be integrally formed with the lid, otherwise it can be a separate housing that is releasably mounted to the lid. The sprayer may be configured to spray the cleaning solution at a predetermined interval. For instance, the sprayer may be configured to spray the solution once a day, or more or less frequently as may be desired. Otherwise, the sprayer may be configured to spray the cleaning solution upon receipt of a manual or virtual command, such as by a pressing a button or otherwise providing instruction to dispense solution. The sanitization device may also include an electronic board, as well as a battery that is connected to the electronic board and the sprayer. The electronic board may provide a command to the battery to activate the sprayer. Additionally, the housing may include a plurality of compartments, which may house one or more of the solution, the battery, and the electronic board. Additionally, a container that contains the solution may be removably insertable into one of the plurality of compartments. In other embodiments, a plastic pod that contains the solution may be removably insertable into one of the plurality of compartments. Further still, the sprayer may include a tube, at least one nozzle connected to the tube, and a valve that is associated with the nozzle. The valve may be opened to dispense the solution from the nozzle. The cleaning solution is configured to kill bacteria within the garbage can, prevent exposure to microorganisms, and minimize the odor within the garbage can.

According to another aspect of the present invention, a method of using a sanitization device for a garbage can includes the steps of installing a housing to an interior of the garbage can, spraying a solution from the housing into the interior of the garbage can, and replacing the solution once the solution is depleted. Additionally, an adjustable nozzle may be rotated between two or more positions relative to a container containing the solution. For instance, the adjustable nozzle may have a first position where the solution is dispensed in a cone of spray of approximately 70 degrees, a second position where the solution is dispensed in a cone of spray of approximately 40 degrees, and a third position where the solution is dispensed in a cone of spray of approximately 20 degrees. The method may also include the steps of disengaging a tab configured to hold the container and nozzle in place relative to the housing, removing the container and adjustable nozzle, replacing the same, and reengaging the tab to hold the replacement container and adjustable nozzle in place. The method may also include the step of spraying the solution from the housing into the interior of the garbage can approximately every twenty-four hours. The method may also include the step of spraying the solution from the housing upon manual or virtual command. Additionally, the method may include the step of mounting the housing to an underside of a lid of the garbage can. Further still, the method may include the steps of providing a signal from an electronic board, providing power from a battery, and activating a valve to enable distribution of the solution from the sprayer.

According to another aspect of the present invention, another method is provided where a first channel of an adjustable nozzle is engaged with a shaft extending from a container containing solution, after which a volume of liquid is sprayed through the first channel and out of the adjustable nozzle about a first orifice. The shaft can be disengaged from the first channel, at which point the shaft is then engaged with a second channel of the adjustable nozzle, and then a volume of the solution is sprayed through the second channel and out of the adjustable nozzle about a second orifice. As described throughout, the first orifice and the second orifice have different spray patterns.

According to another aspect of the present invention, a sanitization device is provided for a garbage can that includes a housing containing a cleaning solution, at least one sprayer contained within the housing that is configured to dispense the cleaning solution into the garbage can, and a power supply and electronic board configured to enable and disable the at least one sprayer. In certain embodiments, the housing is formed in the lid of the garbage can. In other embodiments, the housing is removably connected to the lid, for instance using a mount, a fastener, or an adhesive. Further still, the device may include a level sensor. In the event that the level sensor does not detect that the housing is substantially horizontal, the sprayer can be disabled. To the contrary, when the level sensor detects that the housing is substantially horizontal, the sprayer can be enabled.

These, and other aspects and objects of the present invention will be better appreciated and understood when considered in conjunction with the following description and the accompanying drawings. It should be understood, however, that the following description, while indicating preferred embodiments of the present invention, is given by way of illustration and not of limitation. Many changes and modifications may be made within the scope of the present invention without departing from the spirit thereof, and the invention includes all such modifications.

BRIEF DESCRIPTION OF THE DRAWINGS

A clear conception of the advantages and features constituting the present invention, and of the construction and operation of typical mechanisms provided with the present invention, will become more readily apparent by referring to the exemplary, and therefore non-limiting, embodiments illustrated in the drawings accompanying and forming a part of this specification, wherein like reference numerals designate the same elements in the several views, and in which.

Figure 1:
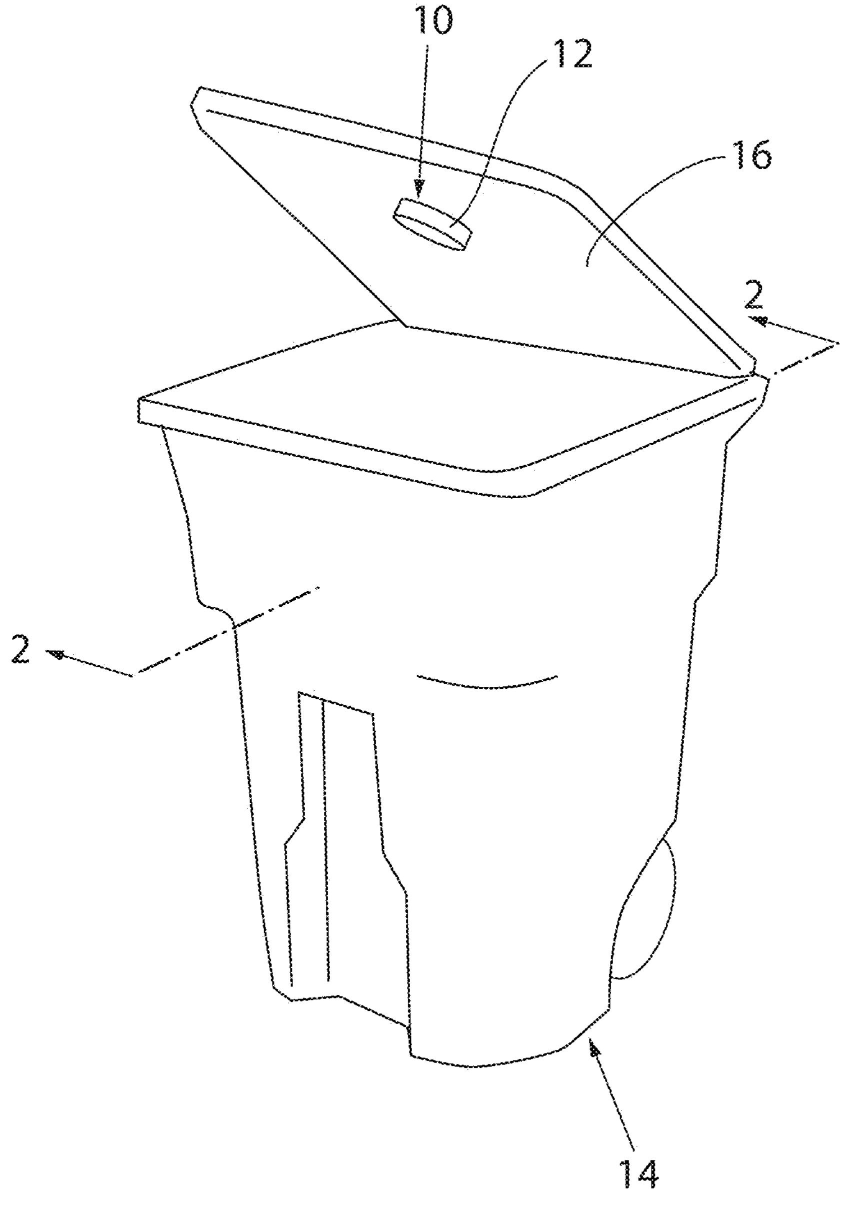
FIG. 1 illustrates a perspective isometric view of a sanitary device for garbage can lids mounted to the underside of the can lid.
Figure 2:
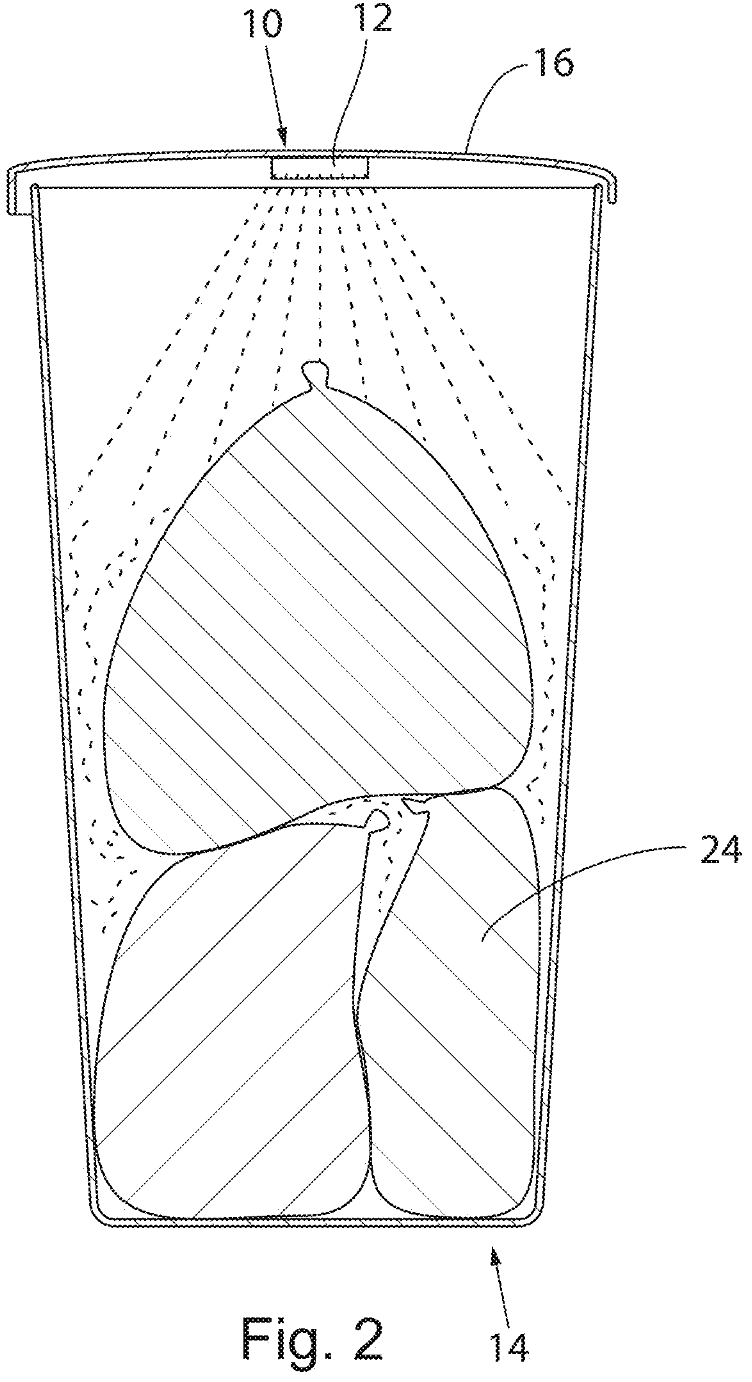
FIG. 2 illustrates a cross sectional view of the garbage can of FIG. 1 about line 2-2 having the sanitary device mounted to the lid while it dispenses a cleaning solution within the garbage can.
Figure 3:
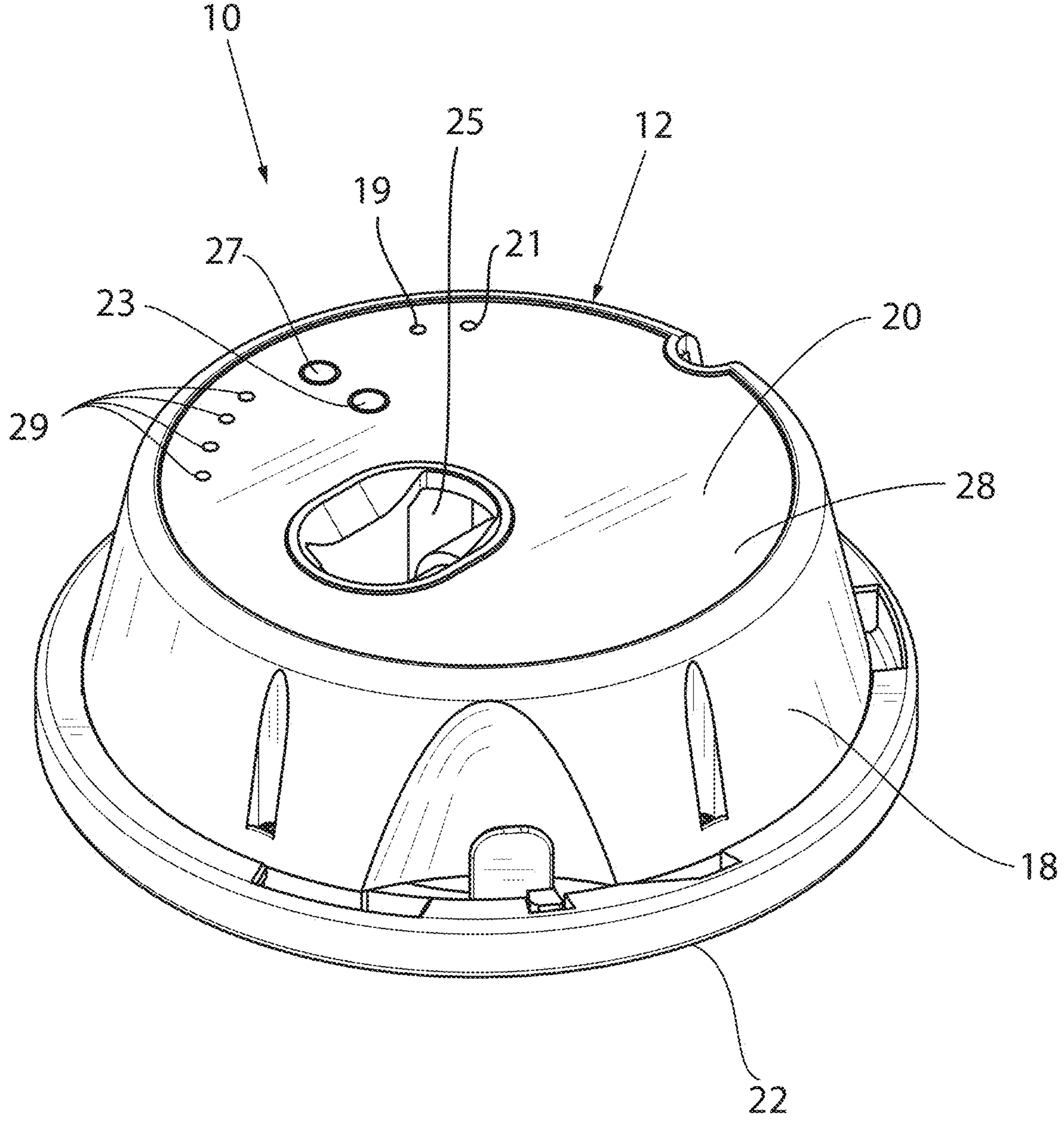
FIG. 3 illustrates a perspective isometric view of the sanitary device.
Figure 4:
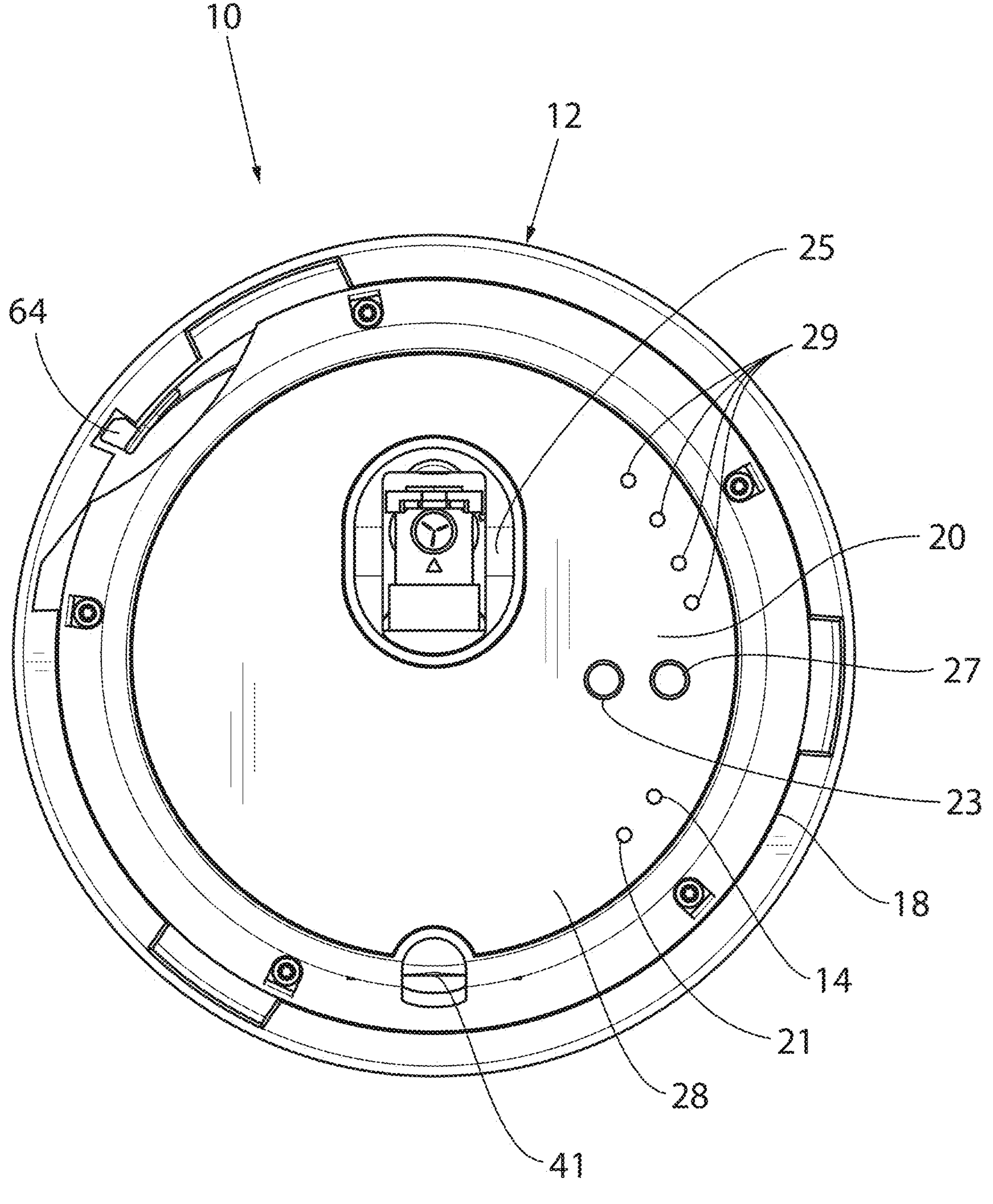
FIG. 4 illustrates a top plan view of the sanitary device.
Figure 5:
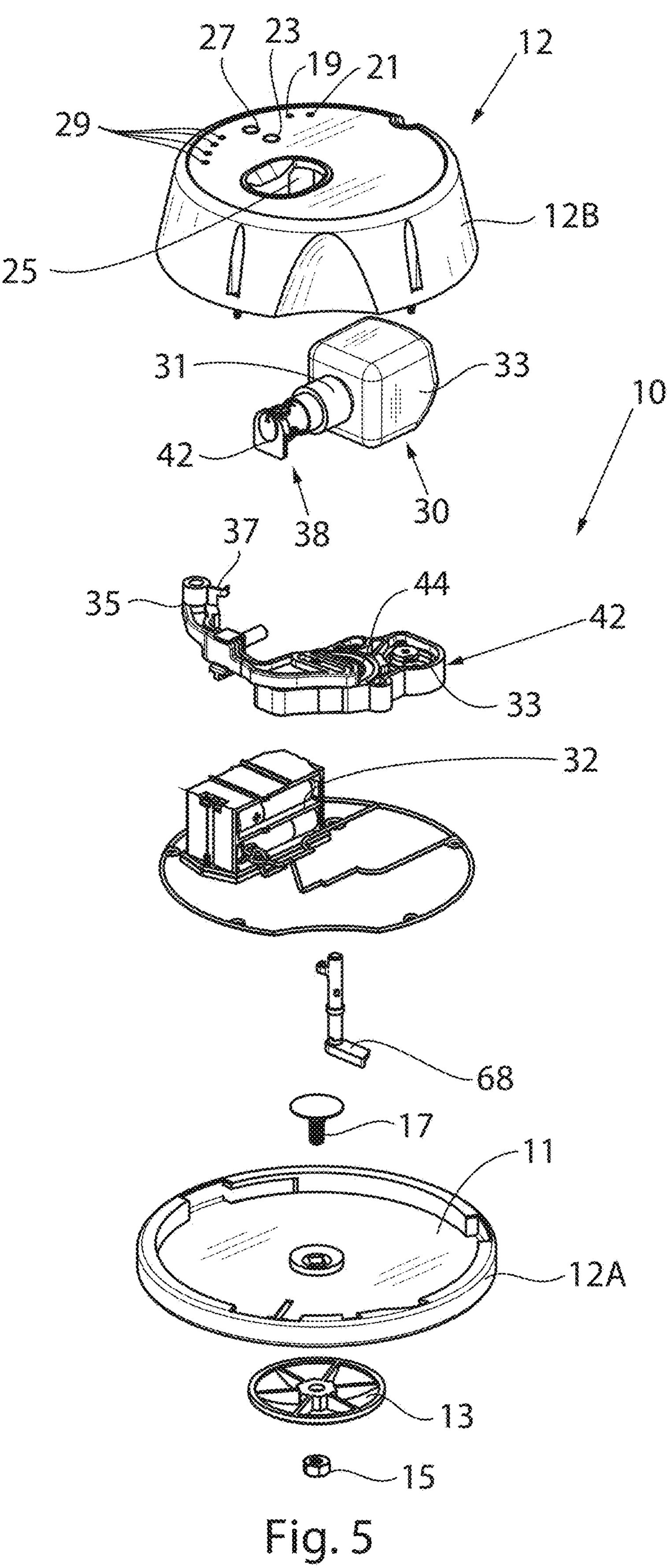
FIG. 5 illustrates an exploded perspective view of the sanitary device.

In describing the preferred embodiment of the invention which is illustrated in the drawings, specific terminology will be resorted to for the sake of clarity. However, it is not intended that the invention be limited to the specific terms so selected and it is to be understood that each specific term includes all technical equivalents which operate in a similar manner to accomplish a similar purpose. For example, the word connected, attached, or terms similar thereto are often used. They are not limited to direct connection but include connection through other elements where such connection is recognized as being equivalent by those skilled in the art.

DESCRIPTION OF PREFERRED EMBODIMENTS

The present invention and the various features and advantageous details thereof are explained more fully with reference to the non-limiting embodiments described in detail in the following description.

The present invention is directed to a sanitary device that can be located within a garbage can to improve the conditions of the interior of the garbage can and to address one or more common issues within garbage cans, including but not limited to adverse smells, germs, bacteria, pests, and microorganisms. For instance, the device can serve one of many functions, including, minimizing growth and spread of bacteria and germs, minimizing odors associated with the interior of the garbage can, improving the sanitization conditions of the interior of the garbage can, reducing exposure of microorganisms, deterring pests from entering the garbage can, eliminating pests that enter the garbage can, and the like. While the description below and the attached figures illustrate the device as being a puck-shaped device that is releasably mounted to the underside of a lid of the garbage can, the device could similarly be in any desired shape or size. Alternatively, the device may be formed directly into the garbage can. Additionally, the below description is related specifically to outdoor garbage cans, but the device could similarly be used with indoor garbage cans, dumpsters, as well as other containers used to house a variety of different objects, including but not limited to recyclable materials, yard waste materials, animal waste materials, or any other materials, all of which will be collectively referred to as garbage cans herein for ease of reference. Further, the device is shown and described as being mounted to the underside of the lid. While this configuration has a number of benefits, such as allowing gravity to help distribute the sanitizing and scented material contained within the device and being less susceptible to dislodgement when garbage is inserted therein, the device could similarly be mounted elsewhere. Also, while the present application is directed to a device to sprays material, the present invention could be used in combination with a number of compatible technologies associated with cleaning and sanitization of garbage cans, including the Disposable Pads described in U.S. Pat. No. 12,006,139, the entire contents of which are incorporated herein by reference.

The present device 10 includes a housing 12 that is mountable relative to a garbage can 14. Again, the device 10 could alternatively be formed directly into the lid 16 of the garbage can 14 such that no mounting would need to occur. The illustrated housing 12 is of two piece construction, with a top housing piece 12A and a bottom housing piece 12B. When assembled, the top housing piece 12A and the bottom housing piece 12B having locking features that mate to form a custom seal.

As mentioned above, the housing 12 shown in the figures is mounted to the lid 16 of the garbage can 14, although it could similarly be mounted elsewhere. In the embodiment shown in the figures, and more specifically FIG. 13, a mounting plate 11 is used in combination with a backer plate 13, bolt 15, and screw 17. The backer plate 13 may be located on the exterior of the garbage can 14 lid 16, with the mounting plate 13 and remaining components of the device 10 on the interior of the garbage can 14. The housing 12 may be twisted to lock into place relative to the lid 16. When a user needs to remove the housing 12, a tab 64 is compressed, after which the housing 12 can be twisted and removed. Such a configuration allows the device 10 to be firmly and easily mounted to the lid 16. Of course, the device 10 could also be mounted to the lid 16 using the mounting plate 11 and backer plate 13 in combination with other mounting components as will further be described below.

Alternatively, the housing 12 may be mounted to the garbage can 14 using any number of other different mounting mechanisms, including for instance high strength adhesive, clips, hooks, belts, hook-and-loop VELCRO fasteners, and the like. In certain embodiments, the high strength adhesive is preferred, as it helps to ensure the housing 12 remains mounted despite the lid 16 being repeated opened and closed, as well as being slammed when the garbage can 14 is emptied. In other embodiments, other devices such as clips, hooks, belts, and hook-and-loop VELCRO fasteners may be preferred as it would allow the housing 12 to be removed from time to time as needed. The housing 12 can be removable mounted to the garbage can 14, allowing it to be quickly and easily removed in order to install it to another garbage can, removed for cleaning purposes and then reinstalled, removed to refill with the cleaning material, or for any other desired reason.

Once installed, the housing 12 is secured to the garbage can 14. For instance, the mounting provides sufficient securement to the lid 16 such that the housing 12 remains in place despite repeated opening and closing of the lid 16, which oftentimes done with sufficient force due to slamming of the lid 16 due to gravity. Alternatively, a mounting plate may be secured to the lid 16, after which the housing 12 can repeatedly be mounted and dismounted from the lid 16 to increase the ease with which additional solution or batteries may be installed.

The illustrated housing 12 is in the shape of a puck, that is generally cylindrical with a sidewall 18, a bottom side 20, and a top side 22. As shown, the top side 22 is formed in the mounting plate 11. As mentioned above, the housing 12 could take any number of different shapes, although a simplified and streamlined housing is desired. The housing 12 includes at least one opening 25 formed therein. For instance, one or more openings 25 may be formed in the sidewall 18 or the bottom side 20. Where the housing 12 is mounted to the lid 16, the opening 25 is directed in a generally downward direction towards the location where the garbage bags 24 are located. This enables material contained within the housing 12 to be sprayed outwardly, after which gravity helps to move the material downwardly onto and around the bags 24 as will further be described below. Similar results would occur where the device 10 is formed directly into the lid 16.

The housing 12 is preferably made of a hard, durable material such as plastic. Additionally, the housing 12 is preferably waterproof or substantially waterproof in order to maintain operability of electrical components contained within the housing 12. This may occur using a gasket to seal the electronic components. In this way, the device 10 can be used for extended periods of time, with other components being replaced if needed.

The housing 12 may include one or more cavities 26 configured to hold various components. For instance, the housing 12 may have a single cavity that hold all interior components that will be further described below. Otherwise, the housing 12 may have a separate cavity for each of the interior components. A cover 28 may be provided that secures the interior components within the cavity or cavities 26. Where the device 10 is formed directly into the lid 16, the cover 28 is removable to access the interior components, because the remainder of the housing is formed with the lid 16.

The housing 12 may also include various light indicators to communicate with users, such as a battery indicator light 19 that notifies a user when the battery level is low, as well as a spray indicator light 21 that notifies a user when the amount of spray is low. The device 10 the total number of sprays, and once a predetermined number of sprays have been completed, the spray indicator light 21 is activated. Additionally, a window 41 may be provided that allows a user to see within the container, and when no solution is contained therein, the container can be refilled. Further still, a variety of indicators 29 may be provided that show the amount of spray that will be dispensed each time the device 10 is activated. Further still, a fill sensor may be provided that monitors how high the garbage bags 24 are stacked within the garbage can 14. For instance, proximity sensors, ultrasonic sensors, and reflective sensors could be used. In the event that the bags 24 are stacked above a maximum height, use of the device 10 will temporarily be terminated until the garbage can 14 is emptied. Furthermore, various controls such as switches or buttons 23, 27 may be provided on the housing 12, for instance a booster switch that provides additional spray, a mode switch that changes the amount of spray provided, an interval switch that enables a user to quickly and easily change the interval within which the solution is sprayed, and any other switches to customize use of the device 10.

Figures 8, 9:
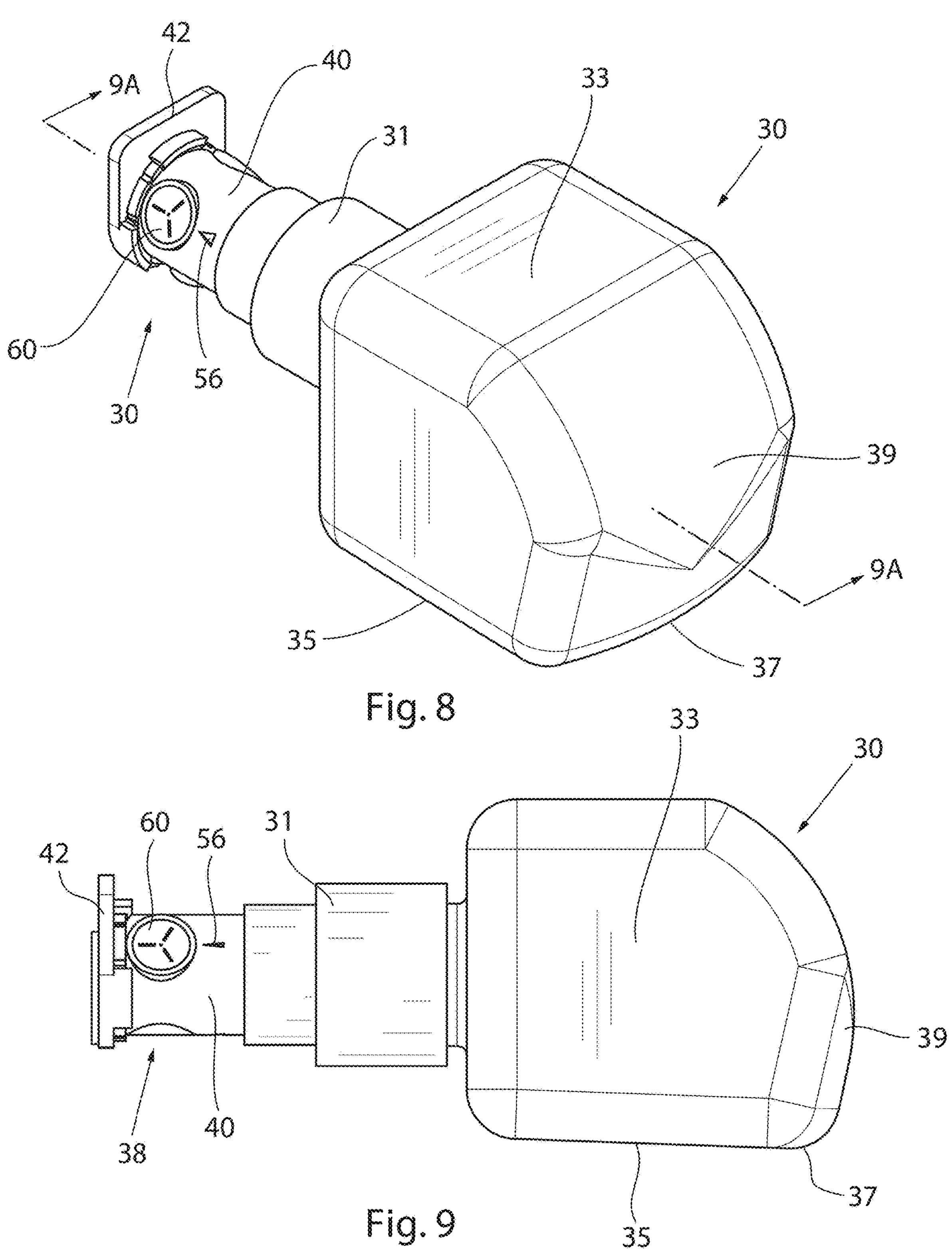
FIG. 8 illustrates a perspective isometric view of a cannister and the adjustable dispenser of the sanitary device.
FIG. 9 illustrates a side elevation view of the cannister and adjustable dispenser.
Figure 9A:
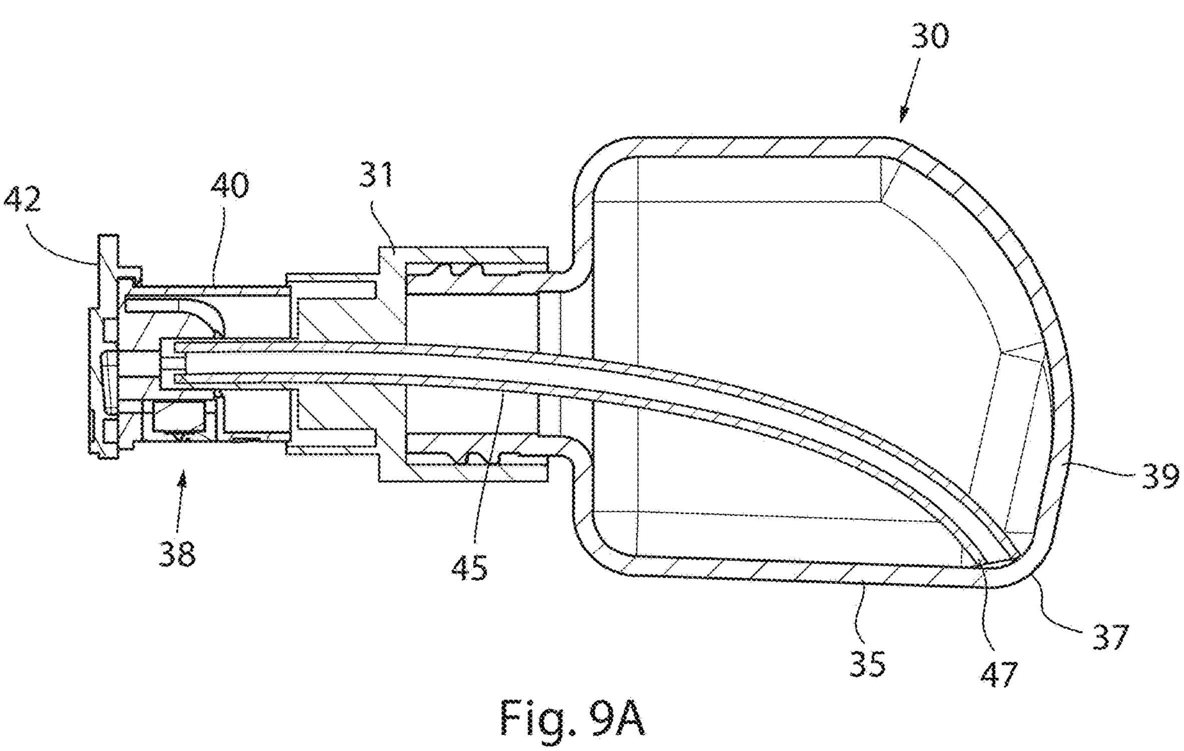
FIG. 9A illustrates a side elevation sectional view of the interior of the cannister and adjustable dispenser.

In terms of interior components, the housing 12 holds a container 30 that holds a liquid or gaseous solution that can be sprayed into the interior of the garbage can 14. The container 30 is shown in isolation in FIGS. 8-9A. The container 30 has a bottle-shaped design including a neck section 31 and a reservoir 33. The reservoir 33 has a bottom side 35. As shown, the bottom side 35 is oriented at a slight angle away from the neck relative to the horizontal. As a result of this inclination of the bottom side 35, liquid contained within the reservoir is automatically pooled towards a far edge 37 of the reservoir 33 that is the lowest point of the container 30, which makes it easier to collect and spray the liquid out of the reservoir 33 to maximize use of the cleaning solution before the reservoir 33 needs to be refilled. Further still, the end wall 39 of the container 30 may similarly be arched so as to funnel the liquid to the far edge 37. As can better be seen in FIG. 9A, which is a cross sectional view of the assembly from FIG. 9, a tube 45 extends from the nozzle 38 towards the container 30. More specifically, the tube 45 extends initially substantially horizontally along the length of the nozzle 38 and a portion of the container 30, after which in slopes downwardly towards the far edge 37 of the reservoir 33. In this way, an end 47 of the tube 45 is directed towards the location where the liquid pools at the far edge 37 to maximize the amount of solution that can be collected by the tube 45.

Figure 10:
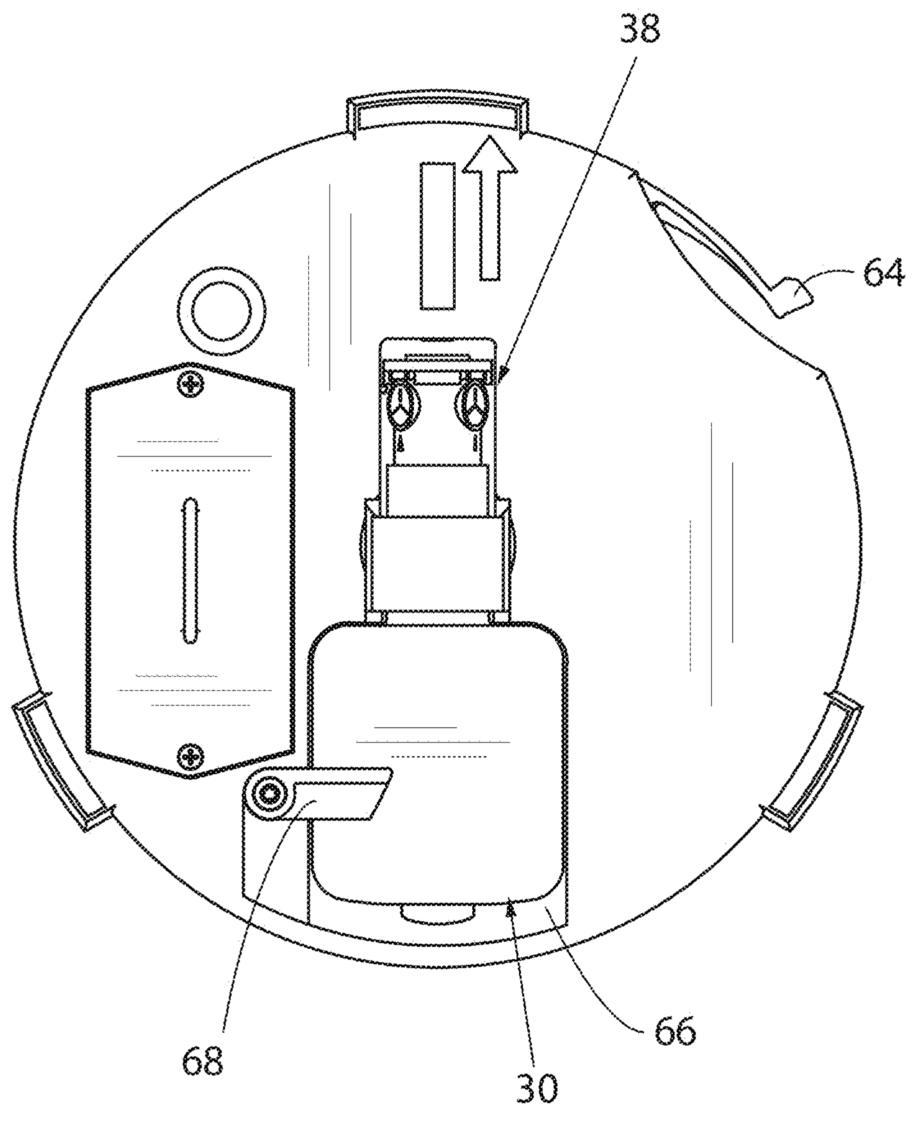
FIG. 10 illustrates a bottom plan view of the sanitary device.
Figure 11:
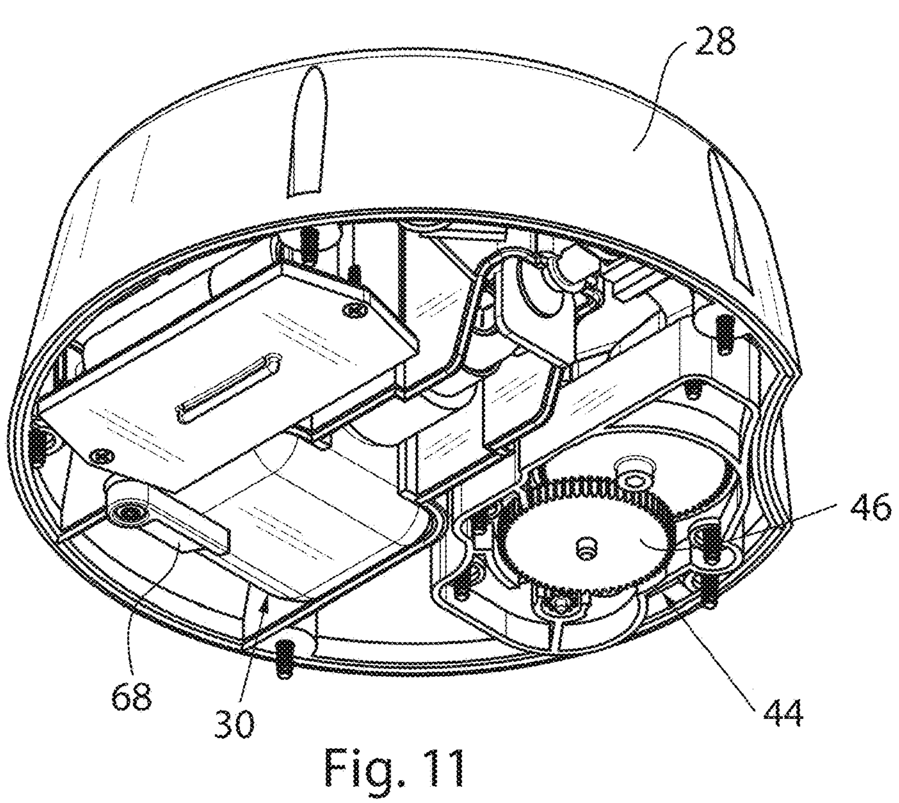
FIG. 11 illustrates a bottom isometric view of the sanitary device with a bottom panel removed.

Additionally, the device 10 may include an adjustable nozzle 38. A first embodiment of the adjustable nozzle is shown in isolation in FIGS. 7 and 8, and mounted to the container 30 in FIGS. 9 and 10. The adjustable nozzle 38 can be moved between multiple position in order to customize operation of the device. More specifically, the illustrator adjustable nozzle 38 is configured to be rotated between multiple positions in order to adjust the range of spray from the nozzle 38. Even more specifically, the adjustable nozzle 38 can be rotated between multiple positions in order to manipulate the spray radius of solution out of the nozzle 38. As shown, the adjustable nozzle 38 is movable between three settings, although of course the nozzle 38 could be movable between only two settings, or more than three settings, as may be desired. As shown, the adjustable nozzle 38 includes a base 40 that is configured to be secured to the neck 31 of the container 30, as well as a side plate 42 that is rotatably connected to the base 40. The base 40 includes multiple fluid passageways 44, 46, 48 associated with the various potential positions. Additionally, the side plate 42 includes a separate passageway 50 that provides a bridge with the selected passageway 44, 46, 48. Additionally, the side plate 42 can include an indicator 52, as shown an arrow, and the base 40 can include multiple indicators 54, 56, as shown arrows (a third indicator would be located on the far side not visible in FIG. 7). A user can align the side plate 42 indicator with the desired base indicator 54, 56 which can identify the specific setting being selected.

Figures 6, 7:
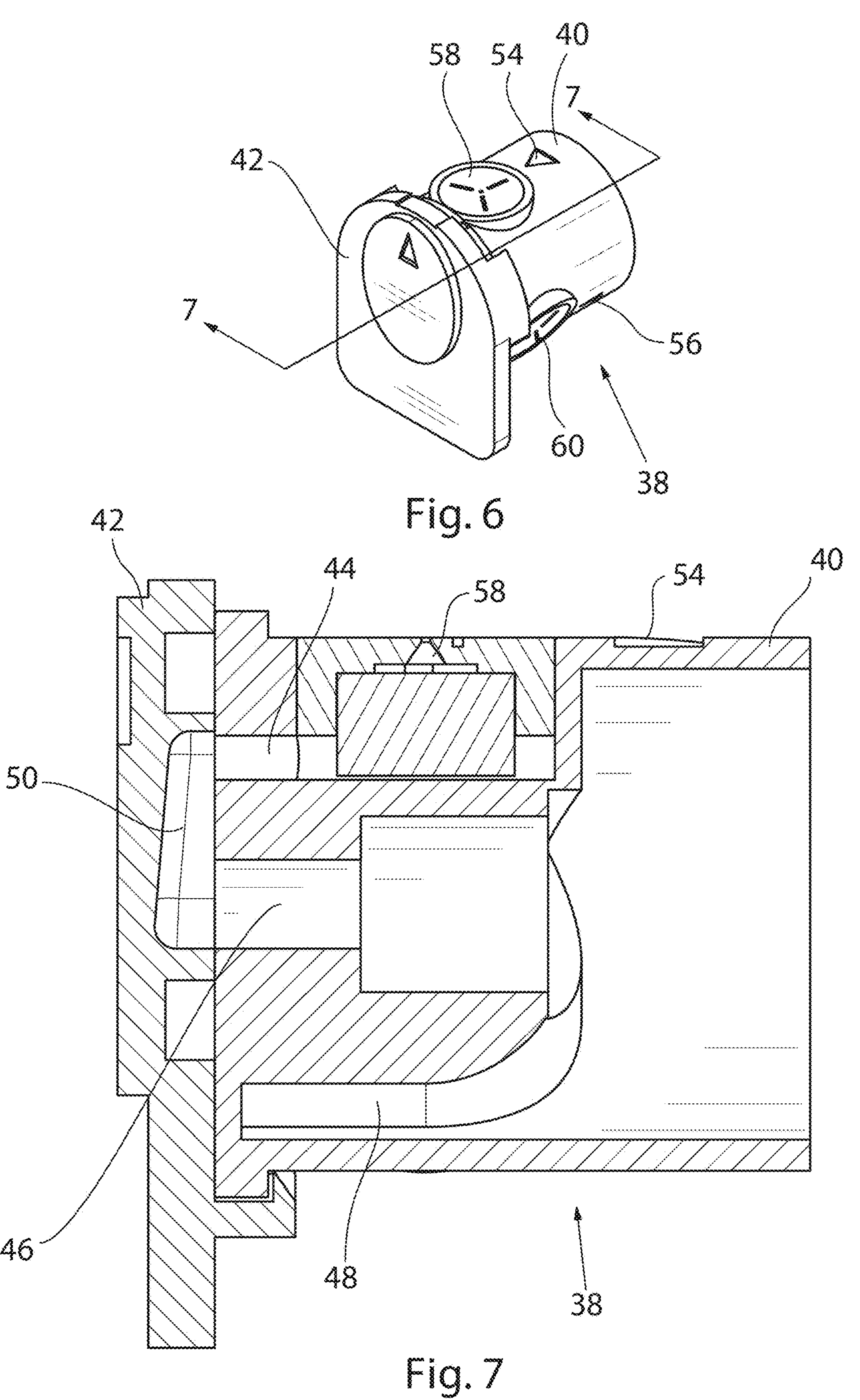
FIG. 6 illustrates a perspective isometric view of an adjustable dispenser used with the sanitary device.
FIG. 7 illustrates a cross sectional view of the adjustable dispenser of FIG. 6 taken about line 7-7.

Additionally, an associated sprayer 58, 60 is formed in the base 40 of the nozzle 38 adjacent to the indicator 54, 56 (again, a third spray nozzle would be located on the far side not visible in FIG. 7). Each sprayer 58, 60 is connected to the container 30 and is configured to deliver solution from the container 30 to the garbage can 14. A valve or other flow restrictive device may be located within the nozzle 38 or the sprayers 58, 60. Flow of the solution out of the sprayer 58, 60 is initially restricted. Thereafter, the valve may be opened to initiate flow of the solution out of the sprayer 58, 60 and into the interior of the garbage can 14. For instance, the device 10 may be set to open the valve and initiate flow of the solution at predetermined intervals, for instance once every 12 hours, once every 24 hours, once every 36 hours, or once every 48 hours. Of course, the intervals could be set as frequently or infrequently as desired. Further still, the device 10 may be set to a standby mode in the event that no spraying is needed, for instance if a user is on vacation and no garbage bags will be deposited into the garbage can 14 for an extended period of time.

Another embodiment of a nozzle 138 that can be used with the device 110 is shown in FIGS. 14-19. In this embodiment, the nozzle 138 is configured to have two different spray patterns based on the orientation in which the nozzle 138 is connected to the container 130 about a pump 140 that includes a shaft 142.

Turning to FIGS. 16-19, the nozzle 138 is shown in isolation with greater detail. The nozzle 138 includes a body 142 having multiple channels formed therein. The illustrated body 142 includes a first end 144 having a first ridge 146 surrounding a first channel 148, and a second end 150 having a second ridge 152 surrounding a second channel 154. A wall 156 is located between the first channel 148 and the second channel 154 to prevent interaction of the two channels.

Additionally, a bottom edge 158 of the body 142 includes two openings 160, 162 formed therein. These openings 160, 162 are in fluid flow communication with the first and second channels 148, 154. More specifically, the first opening 160 is in fluid flow communication with the first channel 148, whereas the second opening 162 is in fluid flow communication with the second channel 154. These openings 160, 162 are configured to receive two plugs 164, 166 having orifices 168, 170 extending therethrough. Of course, additional plugs could similarly be installed having different orifices from the first and second orifices 168, 170. As will further be described below, depending on how the nozzle 138 is mounted to the container 130, solution from the container 130 can either be routed through the first channel 148 and then through the first orifice 168 of the first plug 164, or the solution from the container 130 can be routed through the second channel 154 and then through the second orifice 170 of the second plug 166.

Each orifice 168, 170 has a unique size or diameter. This means that when the solution is moved through the device 110 and out of the first plug 164, a first flow characteristic is achieved, and when the solution is moved through the device 110 and out of the second plug 166, a second flow characteristic is achieved. For instance, the first orifice 168 may have a first, smaller diameter, and the second orifice 170 may have a second, larger diameter. When the solution is routed through the first orifice 168, a smaller flow path or flow angle is achieved, whereas when the solution is routed through the second orifice 170, a larger flow path or flow angle is achieved. This allows a user to adjust the device 110 depending on the desired end result, which may change depending on the garbage can that the device 110 is mounted to, the internal characteristics of the garbage can, the specific problem trying to be remedied (for instance odor elimination, germ elimination, or rodent/pest elimination), or the like. For instance, if used with a smaller garbage can, the user may elect the first orifice 168 so that the solution is sprayed in a more downward direction so as to minimize or avoid having excess solution sprayed on the garbage can walls. In other instances, a user may want the garbage can walls to be sprayed with the solution, in which case the second orifice 170 can be utilized. In other instances, where a large garbage can is involved, the second orifice could similarly be utilized.

Regardless of the specific configuration that the user initially selects, the nozzle 138 can quickly and easily be moved and adjusted as needed. More specifically, the shaft 142 is inserted into either the first channel 148 or the second channel 154. If the user wishes to change the flow characteristics, the nozzle 138 can be disengaged from the shaft 142, the nozzle 138 can be inverted, and the shaft 142 can be inserted into the other channel. The nozzle 138 may include additional components that improve usability of the device. For instance, the nozzle 138 may also include a handle 172 that easy to grip and simplifies the process of removing the nozzle 138 and realigning it with the opposite channel. Additionally, indicia may be included that distinguishes between flow characteristics of the first orifice 168 and flow characteristics of the second orifice 170. As shown, a first indicia 174 may be located adjacent to the first channel 148 that shows a narrow spray pattern, and a second indicia 176 may be located adjacent the second channel 154 that shows a wider spray pattern. This allows a user to quickly and easily distinguish between the two spray patterns associated with the two orifices 168, 170.

Additionally, depending on which channel is selected, the device 110 may be configured for a specific spray sequence. For instance, when the plug having the larger orifice is selected, the device 110 may automatically complete three full sprays, whereas when the smaller orifice is selected, the device 110 may automatically complete two full sprays. Of course, other spray sequences could similarly be employed.

Additionally, the device 10 may be configured to only spray the solution when the garbage can 14 lid 16 is closed, for instance using a sensor 62. For instance, a tilt sensor that would detect if the device 10 is substantially horizontally oriented (in which case the lid 16 is closed), or if the device 10 is substantially vertically oriented (in which case the lid 16 is opened). Other sensors, such as gyroscopes, could similarly be used. Opening of the valve may also or alternatively occur on demand, for instance by pressing a button 27 or other initiator located on or adjacent to the device 10. Further still, activation of the sprayer 58, 60 may occur by any sort of remote communication. For instance, the device 10 may be connected to a remote device, such as a smart phone, a tablet, a computer, or the like, by a website, an application, or the like. This would enable a user to monitor the device 10 away from the garbage can 14, including the settings of the device, the level of the solution, the amount of charge in the battery, etc. Using the application or website, a user can initiate spray in the same way that pressing the button 27 would. Additionally, the user may change the settings remotely, for instance, to increase the frequency of sprays when the weather is warmer, when the contents of the garbage can 14 are particularly prone to odors or germs, and the like. The application or website may also enable automatic ordering or replacement solution or containers 30 when the amount of solution within the container 30 drops beneath a predefined threshold. Other membership or subscription services may be offered through the website or application to enhance usability. Alternatively still, various sensor or other monitoring devices may be mounted within the device 10 or the garbage can 14. When the sensor or other monitoring device detect a given condition, the sprayer 58, 60 may be activated.

Figure 12:
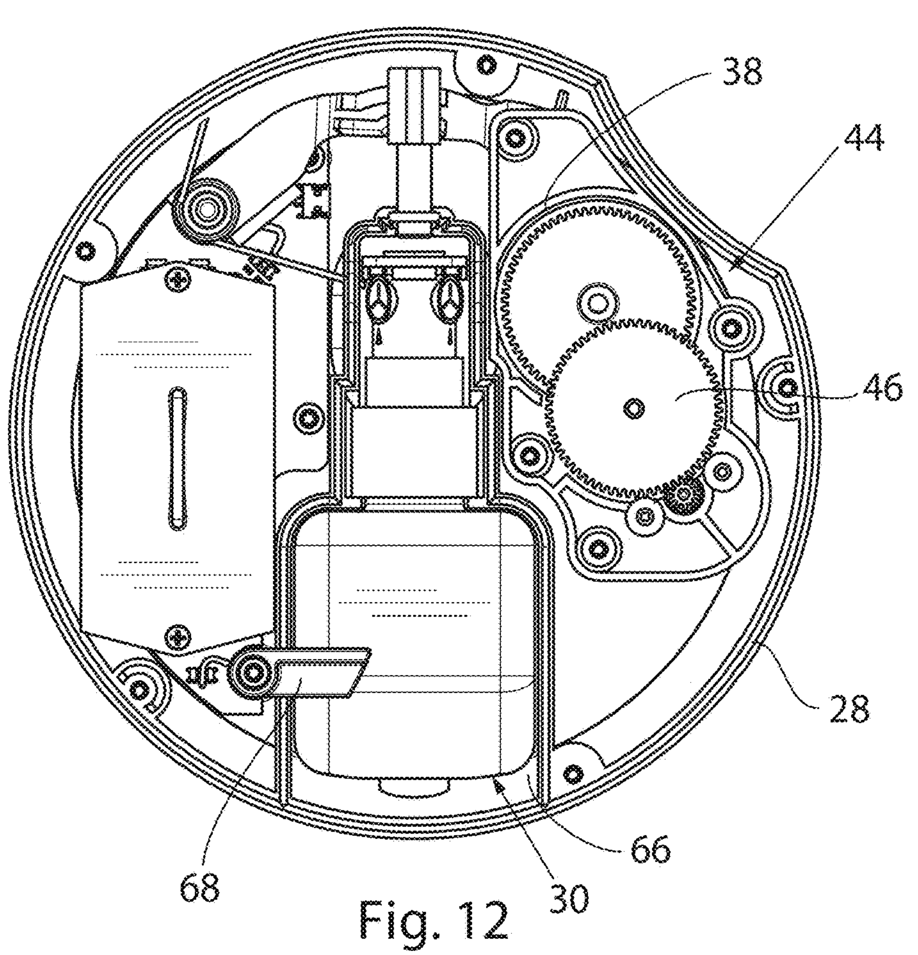
FIG. 12 illustrates a bottom plan view of the sanitary device with the bottom panel removed.
Figure 13:
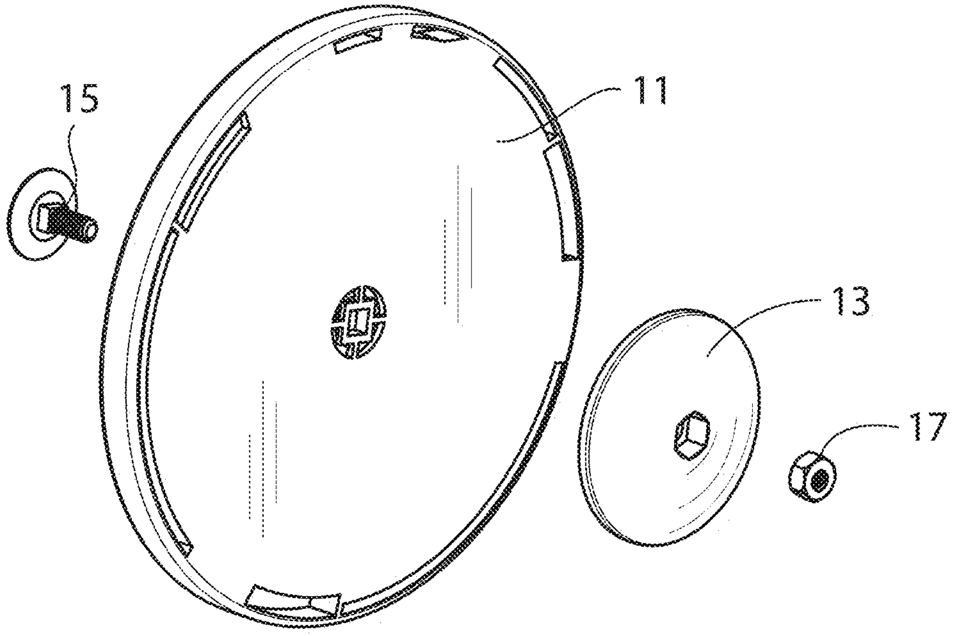
FIG. 13 illustrates an exploded perspective view of a mounting system for the sanitary device.
Figures 14, 15:
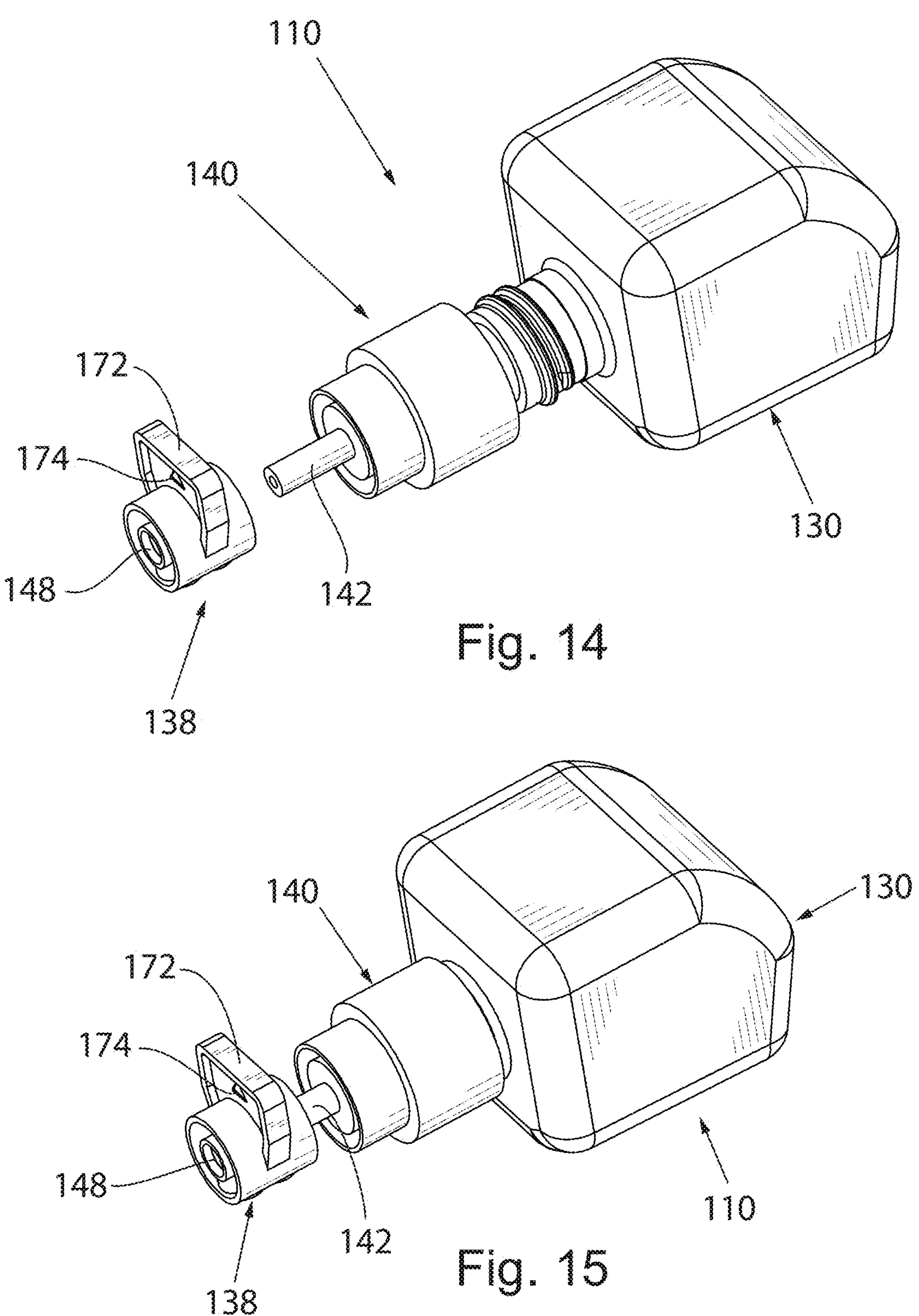
FIG. 14 is an exploded perspective view of another embodiment of the sanitary device.
FIG. 15 is an assembled perspective view of the sanitary device of FIG. 14.
Figure 16:
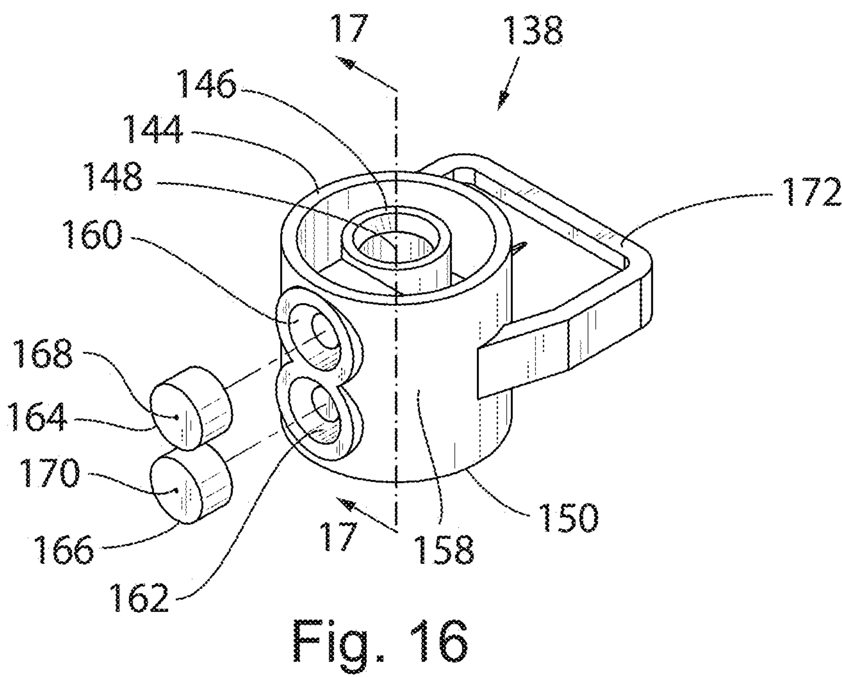
FIG. 16 is an exploded perspective view of a nozzle used with the sanitary device of FIGS. 14 and 15.
Figure 17:
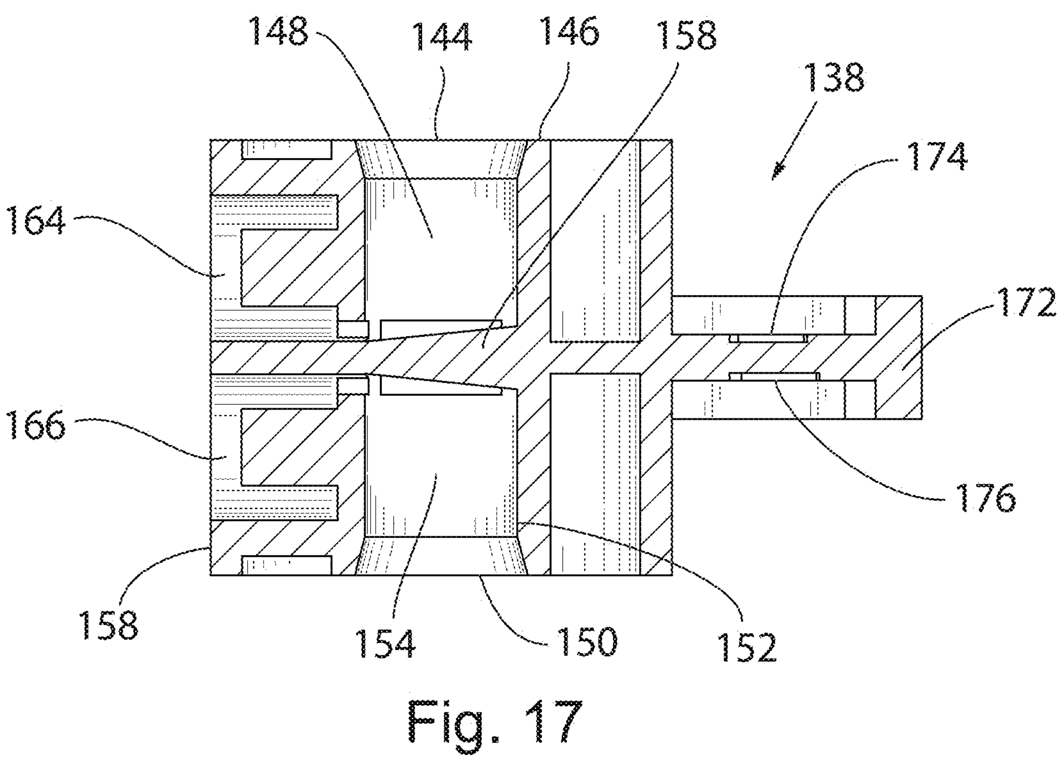
FIG. 17 is a cross-sectional view of the nozzle of FIG. 16 taken about line 17-17.
Figure 18:
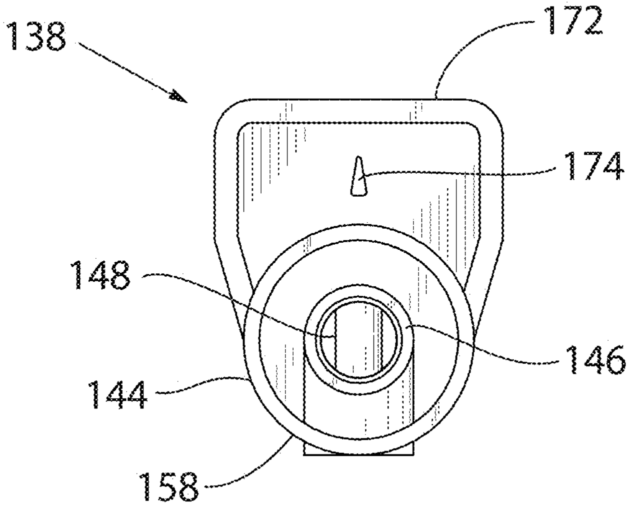
FIG. 18 is a first end elevation view of the nozzle of FIGS. 16 and 17.
Figure 19:
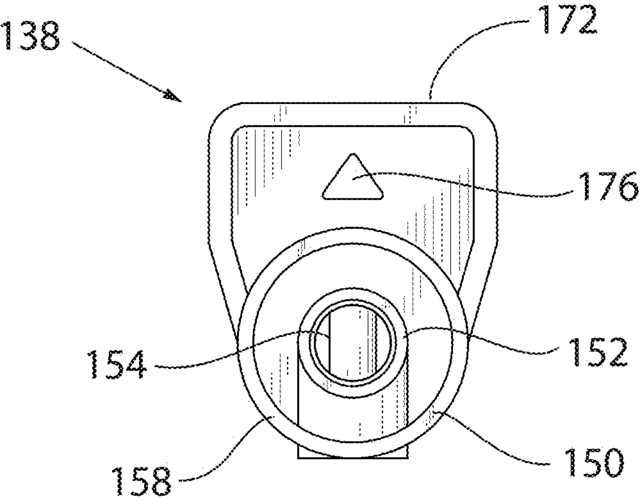
FIG. 19 is a second end elevation view of the nozzle of FIGS. 16-18.

In another embodiment shown in FIGS. 12 and 13, the container 30 could alternatively distribute the solution using the nozzle 38 in combination with a gear system 42. More specifically, the container 30 includes a nozzle 40 that can be compressed to spray materials from within the container 30 out of the container 30. As can be seen, the gear system 42 includes a plurality of gears 44 that are rotated to actuate an actuator 35, which drives a pump head 37 causing the solution to be sprayed out of the container 30. Of course, other nozzle compression systems could similarly be used, include rack and pinion systems, gear trains with extension arms, and crank-sliders.

In the embodiment shown in FIGS. 5-12, the nozzle 38 is movable between a minimum spray radius, a medium spray radius, and a maximum spray radius by aligning the indicator 52 of the side plate 42 with the desired indicator of the base 40. This would allow a user to adjust the spray radius based on the garbage can 14 that the device 10 is being used with. For instance, when the device 10 is used with a relatively small garbage can 14, the minimum spray radius may be selected. If the device 10 is used with a relatively large garbage can 14, the maximum spray radius may be selected. If the device 10 is used with an intermediate sized garbage can 14, the medium spray radius may be selected. This helps to ensure that sufficient spray is provided for a given garbage can 14, without wasting cleaning solution by spraying more than what is required for a given can 14.

By way of example and not limitation, the maximum spray radius may be between approximately 60-80 degrees, more preferably be between approximately 65-75 degrees, and even more preferably approximately 70 degrees. By way of example and not limitation, the medium spray radius may be between approximately 30-50 degrees, more preferably be between approximately 35-45 degrees, and even more preferably approximately 40 degrees. By way of example and not limitation, the minimum spray radius may be between approximately 10-30 degrees, more preferably be between approximately 15-25 degrees, and even more preferably approximately 20 degrees.

As shown, the container 30 and nozzle 38 are mounted to the housing 12. More specifically, an opening 66 is formed in the housing 12 that is configured to receive the container 30 and nozzle 38. Once the container 30 and nozzle 38 are appropriately located, a twist tab 68 is rotated so that it holds the container 30 in place relative to the housing 12. The twist tab 68 can similarly be rotated in the opposite direction when the container 30 is empty and needs to be either refilled or replaced. When the twist tab 68 is rotated to remove the container 30, the sensor measuring the contents of the replacement container 30 can be reset.

The liquid or gaseous solution used in the container 30 can be selected from solutions capable of improving the interior of the garbage can 14, for instance, by deodorizing various smells contained within the garbage can 14, or killing or neutralizing any germs, bacteria, and microorganisms. By way of example and not limitation, ZETRISIL cleaning solution may be used. Specific solutions can also be selected depending on the types of materials that are most commonly contained within the garbage can 14. For instance, if a specific garbage can 14 typically contains a certain material that is particularly susceptible of growth of a specific germ, bacteria, and microorganism, and specific solution can be selected. Additionally, the solution may be selected to either deter pests, including animals or insects, from entering the garbage can 14. Alternatively, the solution may be selected to eliminate the pests, such that when the garbage can 14 is emptied, the pest is disposed of with the remaining contents of the garbage can 14. Of course, the solution may perform multiple functions at once, including for instance eliminating pests while minimizing associated odors, as well as germ, bacteria, and microorganism growth.

Additionally, multiple containers may be included in the housing 12 that contain different solutions that can either be separately sprayed, mixed prior to spraying, or sprayed at the same time. For instance, one container may contain a solution that deodorizes the garbage can 14, whereas a second container may contain a solution that kills or neutralizes germs, bacteria, and microorganisms and/or deters or eliminates pests. When at least one container 30 runs out of solution, it can either be removed and refilled, or removed and replaced with a new container of solution. Additionally, a sensor may indicate when the level of solution is low and needs to be replaced. This may be communicated to the user, for instance using a signal light.

Further still, a level sensor component may be provided. The level sensor component may be used to detect how the housing 12 is oriented relative to the garbage can 14, and more specifically whether it is horizontally oriented. In the event that the sensor does not detect that the housing 12 is level, such as when the lid 16 is in an open position, the sensor will disable activation of sprayer 58, 60. This prevents the spread of the solution outside of the garbage can 14.

The next internal component is a power supply 32. The illustrated power supply 32 is a battery or a plurality of batteries that is connected to a motor 33 or other activation mechanism in order to drive the gears 44 of the gear system 42. Once power is supplied to the motor or other activation mechanism, the valve can be opened or closed. Additionally, an electronic board is provided that instructs the power supply to be activated in order to open or close the valve.

Additionally, a kit may be provided. For instance, one or more housings may be provided, as well as replacement components, such as replacement batteries, as well as bottles, containers, or pods containing solution. The kit may also have other components that would be helpful in maintaining the cleanliness of the garbage can. For instance, Disposable Pads described in U.S. Pat. No. 12,006,139 can be inserted into the base of the garbage can be included in the kit, which would help to maintain the cleanliness of both the bottom of the garbage can by the pad and top of the garbage can by the device.

While the above description provides a number of potential uses of the device, it should be noted that there are virtually innumerable uses for the present invention, all of which need not be detailed here. For instance, although the device is described for use with garbage cans and more specifically outdoor garbage cans, they could similarly be used with other types of containers and devices. All the disclosed embodiments can be practiced without undue experimentation.

Although the best mode contemplated by the inventors of carrying out the present invention is disclosed above, practice of the present invention is not limited thereto. It will be manifest that various additions, modifications and rearrangements of the features of the present invention may be made without deviating from the spirit and scope of the underlying inventive concept. In addition, the individual components need not be fabricated from the disclosed materials, but could be fabricated from virtually any suitable materials.

Moreover, the individual components need not be formed in the disclosed shapes, or assembled in the disclosed configuration, but could be provided in virtually any shape, and assembled in virtually any configuration to improve the efficiency and functionality of the device. Furthermore, all the disclosed features of each disclosed embodiment can be combined with, or substituted for, the disclosed features of every other disclosed embodiment except where such features are mutually exclusive.

It is intended that the appended claims cover all such additions, modifications and rearrangements. Expedient embodiments of the present invention are differentiated by the appended claims.

What is claimed is:

1. A sanitization device for a garbage can comprising:
- a housing;
- a container removably held within the housing and containing a solution; and
- a sprayer contained within the housing configured to dispense the solution into the garbage can;
- wherein the sprayer further comprises an adjustable nozzle further comprising:
  - a first channel; and
  - a second channel;
  - a first orifice in fluid flow connection with the first channel; and
  - a second orifice in fluid flow connection with the second channel;
  - wherein the first orifice disperses solution in a wide spray pattern; and wherein the second orifice disperses solution in a narrow spray pattern.

2. The sanitization device of claim 1, wherein the sprayer further comprises an adjustable nozzle configured to have at least two different spray patterns.

3. The sanitization device of claim 2, wherein the adjustable nozzle is configured to be adjustable between:
- the wide spray pattern; and
- the narrow spray pattern.

4. The sanitization device of claim 1, further comprising a pump extending from the container; and
- a shaft extending from the pump;
- wherein the shaft is configured to be removably inserted into the first channel; and
  - wherein the shaft is configured to be removably inserted into the second channel.

5. The sanitization device of claim 1, further comprising:
- a first plug containing the first orifice associated with the first channel; and
- a second plug containing the second orifice associated with the second channel.

6. The sanitization device of claim 1, wherein the solution is configured to kill bacteria within the garbage can, to prevent exposure to microorganisms, and to minimize odor within the garbage can.

7. The sanitization device of claim 1, wherein the solution is configured to deter animals or insects from entering the garbage can.

8. The sanitization device of claim 1, wherein the solution is configured to terminate animals or insects that enter the garbage can.

9. A sanitization device for a garbage can comprising:
- a container containing a solution;
- an adjustable nozzle connected to the container, the adjustable nozzle adjustable between:
  - a first position having a first spray pattern; and
  - a second position having a second spray pattern different from the first spray pattern;
- a housing configured to releasably receive the container and the adjustable nozzle; and
- a power supply and electronic board configured to enable and disable the adjustable nozzle;
- wherein the adjustable nozzle is configured to dispense the solution into the garbage can.

10. The sanitization device of claim 9, wherein the solution is configured to deter animals and insects from entering the garbage can.

11. The sanitization device of claim 9, wherein the solution is configured to terminate animals and insects that enter the garbage can.

12. The sanitization device of claim 9, wherein the adjustable nozzle further comprises:
- a first channel connected to a first orifice configured to spray the solution in a first spray pattern; and
- a second channel connected to a second orifice configured to spray the solution in a second spray pattern.

13. The sanitization device of claim 12, wherein the first spray pattern is a wide spray pattern; and
- wherein the second spray pattern is a narrow spray pattern.

14. A sanitization device for a garbage can comprising:
- a housing;
- a container removably held within the housing and containing a solution;
- a sprayer comprising an adjustable nozzle having at least two spray patterns contained within the housing configured to dispense the solution into the garbage can;
- a pump extending from the container; and
- a shaft extending from the pump;
- wherein the adjustable nozzle further comprises:
  - a first channel; and
  - a second channel;
- wherein the shaft is configured to be removably inserted into the first channel; and
- wherein the shaft is configured to be removably inserted into the second channel.

15. The sanitization device of claim 14, wherein the adjustable nozzle further comprises:
- a first orifice in fluid flow connection with the first channel; and
- a second orifice in fluid flow connection with the second channel.

16. The sanitization device of claim 15, wherein the first orifice disperses solution in a wide spray pattern; and
- wherein the second orifice disperses solution in a narrow spray pattern.

17. The sanitization device of claim 16, further comprising:

a first plug containing the first orifice associated with the first channel; and a second plug containing the second orifice associated with the second channel.

18. The sanitization device of claim 14, wherein the solution is configured to kill bacteria within the garbage can, to prevent exposure to microorganisms, and to minimize odor within the garbage can.

19. The sanitization device of claim 14, wherein the solution is configured to deter animals or insects from entering the garbage can.

20. The sanitization device of claim 14, wherein the solution is configured to terminate animals or insects that enter the garbage can.

* * * * *